(12) United States Patent
Anderson et al.

(10) Patent No.: US 8,202,507 B2
(45) Date of Patent: Jun. 19, 2012

(54) ASSAY FOR VITAMIN B12 ABSORPTION AND METHOD OF MAKING LABELED VITAMIN B12

(75) Inventors: Peter J. Anderson, Davis, CA (US); Stephen Dueker, Davis, CA (US); Joshua Miller, Davis, CA (US); Ralph Green, Elmacero, CA (US); John Roth, Davis, CA (US); Colleen Carkeet, Silver Spring, MD (US); Bruce A. Buchholz, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 1201 days.

(21) Appl. No.: 11/234,079

(22) Filed: Sep. 23, 2005

(65) Prior Publication Data

US 2006/0110322 A1 May 25, 2006

Related U.S. Application Data

(60) Provisional application No. 60/613,172, filed on Sep. 23, 2004.

(51) Int. Cl.
*A61K 51/00* (2006.01)
*A61M 36/14* (2006.01)

(52) U.S. Cl. ..................................... 424/1.11; 424/1.81

(58) Field of Classification Search .................. None
See application file for complete search history.

(56) References Cited

U.S. PATENT DOCUMENTS

| | | | |
|---|---|---|---|
| 3,060,095 A * | 10/1962 | Stolar ............................. | 514/52 |
| 5,783,387 A | 7/1998 | Lucas et al. | |
| 5,801,161 A | 9/1998 | Merkus | |
| 6,315,978 B1 * | 11/2001 | Grissom et al. ............... | 424/1.53 |
| 6,541,224 B2 * | 4/2003 | Yu et al. ......................... | 435/69.5 |
| 6,613,305 B1 | 9/2003 | Collins et al. | |
| 6,656,709 B1 | 12/2003 | Blanche et al. | |
| 6,783,751 B2 | 8/2004 | Heumann | |

OTHER PUBLICATIONS

Alworth et al. (J. Am. Chem. Soc. 1969, 91, 5662-5663).*
Keck et al. (Arch. Microbiol. 1998, 171, 66-68).*
Aimone-Gastin, et al., "Prospective evaluation of protein bound vitamin B12 (cobalamin) malabsorption in the elderly using trout flesh labelled in vivo with 57Co-cobalamin," *Gut*, vol. 41, pp. 475-479 (1997).
Iida K, Kajiwara M., "Evaluation of biosynthetic pathways to delta-aminolevulinic acid Propionibacterium shermanii based on biosynthesis of vitamin B from D-[1-13C] glucose," *NCBI*, vol. 39 (13): 3666-70 (Apr. 2000).
Klee, George G., "Cobalamin and Folate Evaluation: Measurement of Methylmalonic Acid and Homocysteine vs Vitamin B12 and Folate," *Clinical Chemistry*, vol. 46:8(B), pp. 1277-1283 (2000).
Munder, Michael, et al., "Biosynthesis of vitamin B12 in anaerobic bacteria, Experiments with Eubacterium limosum on the incorporation of D-[1-13C] erythrose and [13C] formate into the 5,6-dimethylbenzimidazole moiety" *Eur, J. Biochem.*, vol. 204, pp. 679-683 (1992).
Renz, Paul, et al., "Biosynthesis of vitamin B12 in anaerobic bacteria, Transformation of 5-hydroxybenzimidazole and 5-hydroxy-6-methylbenzimidazole into 5,6-dimethylbenzimidazole in Eubacterium limosum," *Eur. J. Biochem.*, vol. 217, pp. 1117-1121 (1993).
Roof, David M., et al., "Autogenous Regulation of Ethanolamine Utilization by a Transcriptional Activator of the eut Operon in *Salmonella typhimurium*," *Journal of Bacteriology*, vol. 174, No. 20, p. 6634-6643 (Oct. 1992).
Schulze, Bettina, et al., "Biosynthesis of vitamin B12 in anaerobic bacteria, Experiments with Eubacterium limosum on the transformation of 5-hydroxy-6-methyl-benzimidazole its nucleoside, its cobamide, and of 5-hydroxybenzimidazolylcobamide in vitamin B12" *Eur. J. Biochem.*, vol. 254, pp. 620-625 (1998).
Trzebiatowski, Jodi R., et al., "Purification and Characterization of CobT, the Nicotinate-Mononucleotide:5,6-Dimethylbenzimidazole Phosphoribosyltransferase Enzyme from *Salmonella typhimurium* LT2," *The Journal of Biological Chemistry*, vol. 272, No. 28, pp. 17662-17667 (1997).

* cited by examiner

*Primary Examiner* — Michael G Hartley
*Assistant Examiner* — Melissa Perreira
(74) *Attorney, Agent, or Firm* — Kilpatrick Townsend & Stockton LLP

(57) ABSTRACT

The invention provides methods for labeling vitamin B12 with $^{14}C$, $^{13}C$, tritium, and deuterium. When radioisotopes are used, the invention provides for methods of labeling B12 with high specific activity. The invention also provides labeled vitamin B12 compositions made in accordance with the invention.

8 Claims, 5 Drawing Sheets

ASSAY FOR VITAMIN B12 ABSORPTION AND METHOD OF MAKING LABELED VITAMIN B12

CROSS-REFERENCES TO RELATED APPLICATIONS

This application claims benefit of U.S. provisional application 60/613,172, filed Sep. 23, 2004, which application is incorporated by referenced herein.

STATEMENT AS TO RIGHTS TO INVENTIONS MADE UNDER FEDERALLY SPONSORED RESEARCH AND DEVELOPMENT

This invention was made with Government support under Grant No. GM34804 awarded by the National Institutes of Health. The Government has certain rights in this invention. The United States Government also has rights in this invention pursuant to Contract No. W-7405-ENG-48 between the United States Department of Energy and the University of California for the operation of Lawrence Livermore National Laboratory.

BACKGROUND OF THE INVENTION

Vitamin B12 (cobalamin, or "Cbl") deficiency is a significant public health problem, particularly among the elderly. In the United States, there are 37 million people over age 65 and conservative estimates indicate that 2-3% of this population has or will develop pernicious anemia caused by failure of gastric intrinsic factor production and consequent B12 malabsorption (Chanarin, I. *The megaloblastic anemias, 2nd edition*. "Blackwell Scientific Publications" Oxford (1979); Cannel, R. *Archives of Internal Medicine* 156:1097-1100 (1996)). Other estimates suggest that the prevalence of B12 deficiency may be as high as 30-40% among the elderly due to food B12 malabsorption caused by chronic gastritis, gastric atrophy, and perhaps other unknown causes (Baik, H. W. et al. *Annual Review of Nutrition* 19:357 77 (1999)). In addition, surgical procedures such as gastrectomy and ileal resection, inflammatory bowel disease (Crohn's disease), radiation therapy for cancers of the abdominal or pelvic region, treatment of gastric reflux with H2 blockers such as omeprazole, and bacterial overgrowth in the small intestine, cause B12 malabsorption syndromes. Recently, we and others have observed an apparently high prevalence of B12 deficiency in both children and young adults in diverse locations, such as Guatemala, Mexico, Kenya, and Israel (Rogers, L. M. et al., *FASEB J* 13:A251 (1999); Gielchinsky, Y. et al., *British Journal of Haematology* 115:707-9 (2001); Lindsay, H. Allen, PhD. *Personal Communication*). The causes of B12 deficiency in these populations are unclear, but may be related to a combination of low intake and unrecognized malabsorption.

The classical pathophysiological manifestations of B12 deficiency include megaloblastic anemia and neurological degeneration related to neuronal demyelination (Green, R. et al., *Neurology* 45:1435-40 (1995)). Neurological deficits run the gamut from peripheral neuropathy to depression, cognitive disturbances, and dementia (Savage, D. G., *Baillier's Clinical Haematology* 8:657-78 (1995); Van Goor, L. P. et al., *Age Ageing* 24:536-42 (1995)). Moreover, recent evidence suggests that B12 deficiency may contribute to the risk of vascular disease (related to elevated plasma levels of the vascular risk factor homocysteine) (Refsum, H. et al., *Annu Rev Med* 49:31-62 (1998)), cancer (particularly breast cancer) (Choi, S-W. *Nutrition Reviews* 57:250 60 (1999)), and neural tube defects (spina bifida, anencephaly) (Refsum, H. *British Journal of Nutrition* 85 (supp12):S109-13 (2001)). B12 deficiency may also play a role in the rate of onset of clinical AIDS resulting from HIV infection (Tang, A. M. et al., *Journal of Nutrition* 127:345-51 (1997); Baum, M. K. et al., *AIDS* 9:1051-6 (1995))

The risks of B12 deficiency may be accentuated by folic acid fortification. The importance of recognizing B12 deficiency and conditions that cause B12 malabsorption is magnified by the government-mandated addition of folic acid to the United States food supply since Jan. 1, 1998 intended to reduce the risk of neural tube birth defects. A recent national advisory committee on B vitamin intake has cautioned on the need for increased vigilance to detect B12 deficiency and its causes, particularly among the elderly in the wake of the folic acid fortification initiative (Food and Nutrition Board—Institute of Medicine. *Dietary reference intakes for thiamin, riboflavin, niacin, vitamin B6, folate, vitamin B12, pantothenic acid, biotin, and choline*. National Academy Press, Washington, D.C. (1998)). This is based on the well-recognized observation that folic acid can reverse megaloblastic anemia caused by B12 deficiency while neurological degeneration progresses unabated. This is important because B12 deficiency in the elderly is often not suspected until anemia develops. It is unknown whether the supplemented level of folic acid in the food supply will increase the incidence of neurological damage due to undiagnosed B12 deficiency. Several authoritative sources have cautioned that there is no known safe dose of supplemental folic acid in patients with untreated B12 deficiency (Chanarin, I. *The megaloblastic anemias, 2nd edition*. "Blackwell Scientific Publications" Oxford (1979); Food and Nutrition Board—Institute of Medicine. *Dietary reference intakes for thiamin, riboflavin, niacin, vitamin B6, folate, vitamin B12, pantothenic acid, biotin, and choline*. National Academy Press, Washington, D.C. (1998)). Therefore, the institution of folic acid fortification necessitates increased consideration of B12 status, particularly in older adults.

B12 absorbed across the small intestine enters the circulation bound to a transcobalamin. Ingested B12 is released from food sources by the activity of gastric enzymes aided by the low pH of the stomach maintained by gastric acid (Stabler, S. P. *In: Present Knowledge in Nutrition*, 8th ed. Bowman B A, Russell R M, eds. Washington, D.C.: ILSI (2001)). After its release from food, B12 binds with haptocorrin (also known as "R binder") secreted by the salivary glands. The B12-R binder complex then travels to the small intestine where, in an alkaline milieu, trypsin and other pancreatic proteases degrade the R binder and release the B12. The B12 subsequently binds with the gastric glycoprotein, IF. The IF-B12 complex binds to specific receptors located on the brush border of the ileal mucosa. Following internalization, the B12 molecule is released from IF within ileal enterocytes and enters the portal venous blood bound to transcobalamin II (TC II), one of three B12 carrier proteins in the plasma. TC II is produced in endothelial cells and is responsible for receptor-mediated uptake of B12 by all tissues. Structurally distinct from TC II are the haptocorrins (also known as transcobalamins I and III). These are glycoproteins produced in granulocytes, and appear to play no role in receptor-mediated cellular B12 delivery.

The Schilling Urinary Excretion test has been the standard method of testing for a patient's ability to absorb B12 since its introduction in 1953. The test has four stages. In Stage I, the patient takes an oral dose of B12 labeled with a radioactive isotope of cobalt, such as $^{60}$Co or $^{57}$Co. A period of time, usually 2 to 6 hours, is permitted to pass to allow sufficient time for the labeled B12 to be absorbed into the patient's small intestine. At the end of the period, the patient is given an intramuscular injection of an excess of non-labeled B12 to flush labeled B12 that the patient has absorbed into the intestine out of the patient into the urine. The patient collects all of his or her urine for a 24 hour period (a so-called "complete collection"), and the radioactivity in the urine is then measured. In patients with normal absorption, 8 to 40% of the labeled B12 will appear in the urine, while patients with absorption problems will have less than 8%, or frequently none.

If the amount of radiolabeled B12 in the urine reveals that the B12 has not been absorbed well from the oral dose, the cause for the malabsorption must be determined. Thus, after a sufficient time has passed to permit most of the excess B12 administered in Stage I to be eliminated from the intestinal tract, Stage II of the test is conducted. In this Stage, radiolabeled B12 is administered again, this time with an oral dose of intrinsic factor. Proper absorption indicates that the problem is a lack of intrinsic factor. If the B12 is again not absorbed, the problem could be, for example, bacterial overgrowth with consumption of B12, sprue, celiac disease, or liver disease. Thus, if the Stage II results are abnormal, Stage III is conducted. In this Stage, the patient is put on antibiotics for two weeks and the B12 absorption measured again to see if excess bacterial growth is interfering with B12 absorption. Finally, if absorption is still abnormal, the Stage IV test involves administering pancreatic enzymes in conjunction with radioactive B12 to determine if the malabsorption is due to a lack of these enzymes, another rare cause of B12 malabsorption.

While the Schilling test has been the standard test for decades, its use has become rare. The test is cumbersome, relatively unreliable and expensive. The test requires the use of B12 labeled with radioactive cobalt, which is difficult to procure and to dispose of. Radioactive cobalt emits gamma radiation, a penetrating form of radiation which is only attenuated using very dense protective shielding (often lead); this exposes the patients and medical personnel to a small but quantifiable level of gamma radiation from the labeled B12. Moreover, the urine samples provided by the patients following dosage must be treated as radioactive waste. The increasingly stringent regulation of radioactive waste, the undesirability of subjecting patients to gamma radiation, and the extra handling care required for a gamma emitter all increase the expense of the test and reduce the desirability of administering it.

Additionally, because the first stage of the test involves administering an injection of B12 to the patient, it is necessary to wait a significant time for the B12 from that shot to be eliminated before the patient can be administered a second test to determine whether lack of intrinsic factor is the reason for the deficiency. This waiting period causes problems with patient compliance and, of course, undesirably delays treatment of the underlying condition. Further, since the test is based on urine collection, it is problematic for use with people who have renal problems, since lack of labeled B12 in the urine may reflect renal insufficiency rather than absorption problems. Unfortunately, the prevalence of renal problems tend to be higher in older people, who are also the population who most need to be tested for B12 absorption problems.

In some instances, the problem is that the patient cannot absorb B12 well from food, but can absorb so-called crystalline B12 well. In these instances, the patient can get adequate B12 simply by taking it in pill form, avoiding the need for monthly injections.

B12 labeled with radioactive carbon or hydrogen would be a useful alternative to B12 labeled with radioactive cobalt. $^{14}C$, for example, emits beta particles, rather than gamma radiation, and is thus safer for lab personnel to handle, as well as safer for patients. B12 labeled with carbon or hydrogen is not commercially available. $^{14}C$-labeled B12 was made by Boxer et al. as early as 1951 (Arch Biochem. 30(2):470-1). The B12 was labeled by labeling the cyano group and making cyanocobalamin. Unfortunately, since the cyano-group is cleaved off in the body, B12 labeled in this manner is not useful for metabolic studies or for tracking B12 absorption. B12 can also be labeled with $^{14}C$ by growing bacteria on media labeled with $^{14}C$ and then separating out the B12; unfortunately, in many cases, relatively little B12 is made in comparison to other bacterial metabolic products, resulting in a small amount of radiolabeled B12 and a large amount of radiolabeled waste material. Moreover, even in cases where the organism makes a relatively high percentage of B12 compared to other products, only a small proportion of the B12 is labeled in comparison to the total amount of B12. Since there is a limit to how much B12 can be absorbed even by persons with normal absorption of B12, to be useful, a high percentage of the B12 molecules should be labeled for the results of any studies to be accurate. (The degree to which a substance is labeled is referred to as its "specific activity.") The recommended daily intake of vitamin B12 is 2.4 μg. Larger doses have the possibility of altering the B12 status before a diagnosis can be made, and a dose with a vitamin B12 mass less than 10 μg is therefore desirable, with doses of 5 μg or smaller being desirable. Thus, it is desirable to use B12 with a high specific activity.

It would be desirable to have a radiolabeled B12 that is not labeled with a gamma emitter. It would further be desirable to be able to produce a radiolabeled B12 in a manner that does not create large amounts of radioactive waste in its production in comparison to the amount of labeled B12 and that has high specific activity. It would be further useful to be able to have a test for B12 deficiency that would permit determination of the cause of B12 deficiency. The present invention fulfills these and other needs.

BRIEF SUMMARY OF THE INVENTION

The invention provides methods for labeling vitamin B12, comprising providing a facultative anaerobe bacterium (i) which has a eut operon, (ii) which requires B12 to grow on a medium in which ethanolamine or propandiol is the only carbon source, and (iii) cannot synthesize B12 under aerobic conditions, (b) providing a medium having ethanolamine or propandiol as the only carbon source, (c) providing labeled cobinamide ("Cbi"), or a labeled dimethylbenzimidazole ("DMB"), or both, and (d) culturing the bacterium on said media in the presence of said Cbi and said DMB, under aerobic conditions, thereby resulting in the formation of labeled B12. The bacterium can be a *Salmonella* species. In some embodiments, the *Salmonella* species is *S. enterica*. The label can be, for example, $^{14}C$, $^{13}C$, deuterium, and tritium. The label can be on the DMB.

In other embodiments, the invention provides methods of determining absorption of vitamin B12 in a subject, comprising: (a) administering B12 labeled with $^{14}C$, $^{13}C$, deuterium, or tritium to the subject; (b) taking a blood sample from said subject, (c) subjecting the blood sample to mass spectroscopy and measuring elevation of $^{14}C$, $^{13}C$, deuterium or tritium associated with the labeled B12 above background $^{14}C$, $^{13}C$, deuterium, or tritium concentrations, respectively and (d) comparing said concentration of labeled B12 to the concentration of labeled B12 found in subjects with normal B12 absorption. In some embodiments, the mass spectroscopy is accelerator mass spectroscopy. In some embodiments, the label is $^{14}C$ or tritium.

In yet other embodiments, the invention provides methods of studying vitamin B12 metabolism in a subject, comprising: (a) administering B12 labeled with $^{14}C$, $^{13}C$, deuterium, or tritium to said subject; (b) taking a blood sample from said subject, (c) subjecting said blood sample to mass spectroscopy and measuring elevation of $^{14}C$, $^{13}C$, deuterium or tritium associated with the labeled B12 above background $^{14}C$, $^{13}C$, deuterium, or tritium concentrations, respectively and (d) comparing said concentration of labeled B12 to the concentration of labeled B12 found in subjects with normal B12 absorption. The vitamin B12 metabolism can be plasma clearance, turnover rate, enzyme kinetic measurement, or uptake and distribution of the vitamin.

In another aspect, the invention provides a radioactively labeled vitamin B12 composition having a specific activity of at least about 100 mCi/mol wherein the label is $^{14}C$, and physiologically acceptable compositions comprising such labeled vitamin B12 compositions. In some embodiments, the radioactively labeled vitamin B12 composition has a specific activity of at least 1 Ci/mol. In other embodiments, the radioactively labeled vitamin B12 composition has a specific activity of at least 10 Ci/mol, often at least 25 Ci/mol or at least 40 Ci/mol. In exemplary embodiments, $^{14}C$-labeled B12 has a specific activity of 50-62 Ci/mol. In other embodiments, the $^{14}C$-labeled B12 has a specific activity of 37 Ci/mol.

B12 compositions of the invention also include tritium-labeled vitamin B12 compositions, and physiologically suitable compositions comprising such tritium-labeled B12 compositions. The specific activity is often at least 25 Ci/mol. Typically, the tritium-labeled vitamin B12 of the invention has a specific activity that is in the range from about 3000 to about 5000 Ci/mol. In some embodiments the specific activity is about 55,000 Ci/mol, e.g., 57,400, Ci/mol.

The invention also provides a labeled vitamin B12 composition that has a nonradioactive label incorporated, e.g., $^{13}C$ or deuterium. Such labeled vitamin B12 compositions typically have at least over 10% of the label incorporated into them. Typically, nonradioactively-labeled B12 molecules of the invention have over 50%, often over 60-70%, and typically 90%-100% incorporated label.

DETAILED DESCRIPTION OF THE INVENTION

I. Introduction

Figure 1:
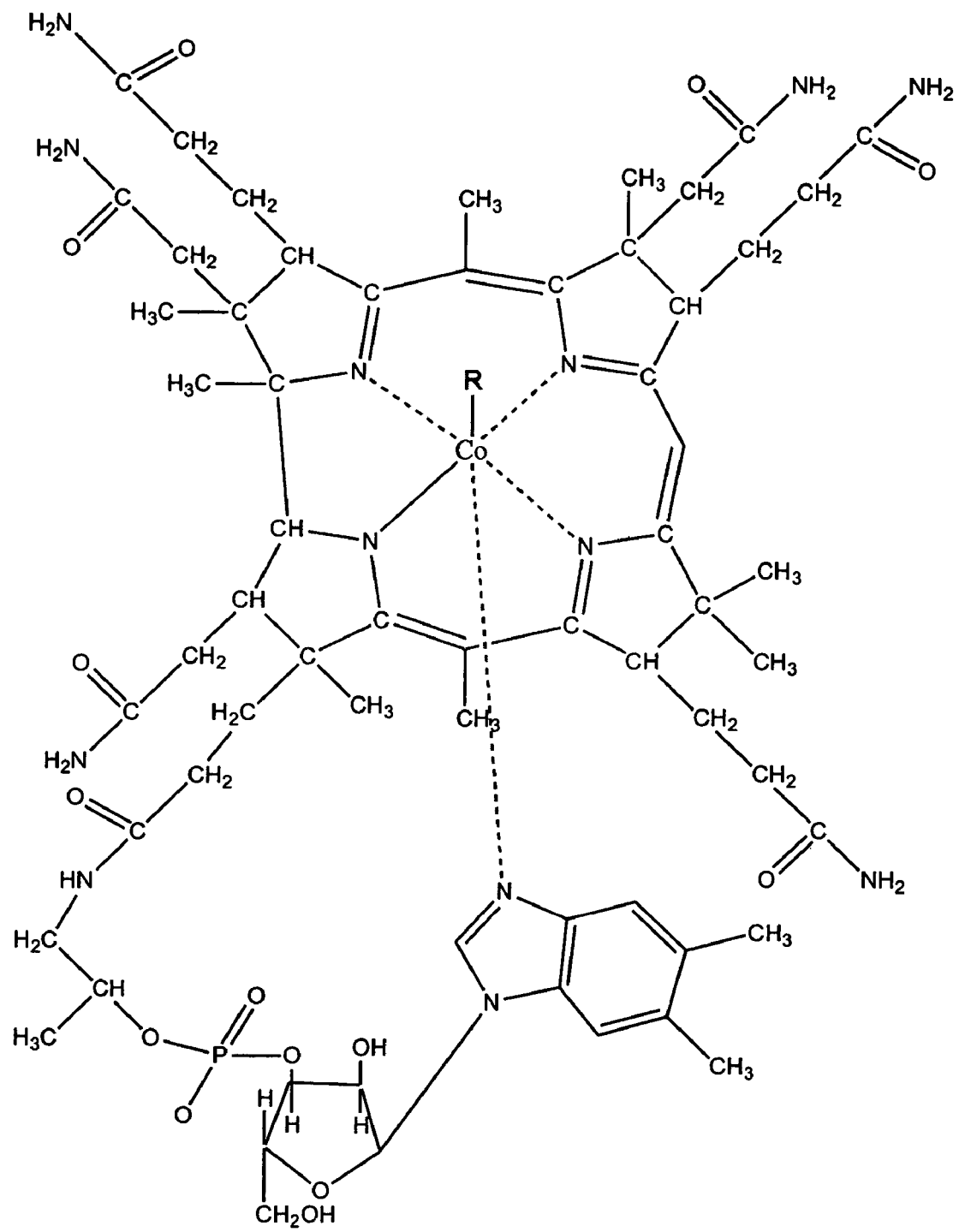
FIG. 1 is a diagram of a B12 molecule. The corrin ring is the structure comprising the cobalt at the core of the molecule, while 5,6-dimethylbenzimidazole is the nucleotide ligand at the lower middle of the figure. The R group is most often methyl, deoxyadenosyl, cyano, or hydroxo.
Figure 2:
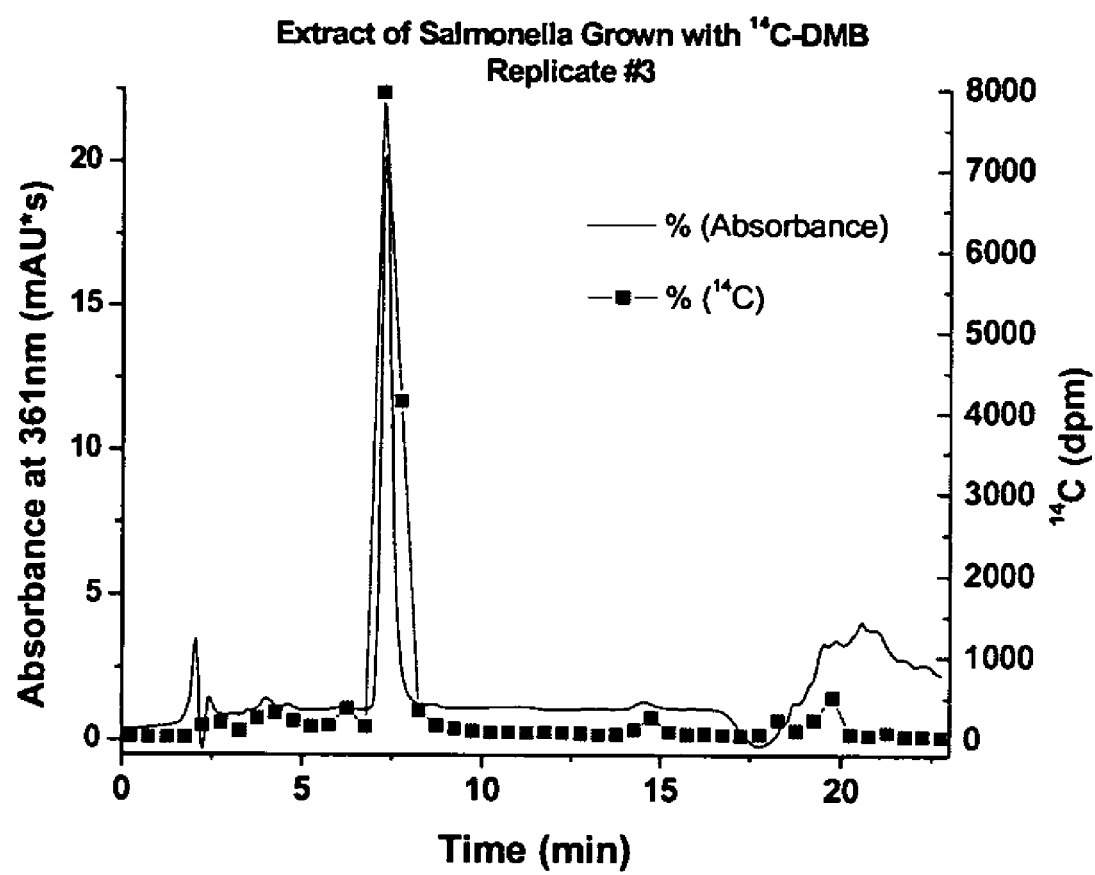
FIG. 2 shows a radiochromatograom of $^{14}C$-vitamin $B_{12}$ from S. typhimurium following growth with $^{14}C$-DMB.
Figure 3:
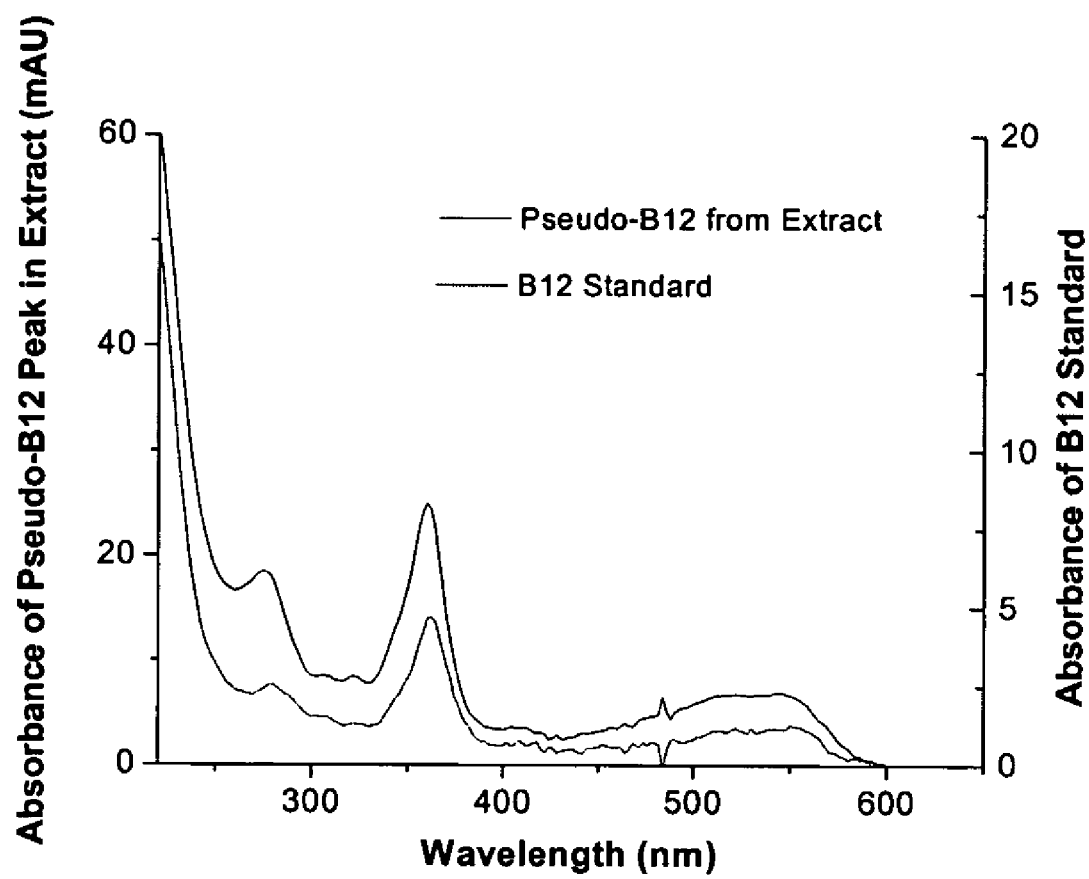
FIG. 3 shows the UV/vis Spectrum of the $B_{12}$ peak from the bacterial extract (upper line) and a vitamin $B_{12}$ standard (lower line).

Surprisingly, the present invention provides methods for producing $^{13}C$- or $^{14}C$, or tritium-radiolabeled vitamin B12 without creating large amounts of radiolabeled waste compared to the amount of B12. The invention provides for labeled B12 with high specific activity, that is, that a high percentage of the B12 molecules are labeled relative to those that are not. Further, the invention provides methods of assaying B12 absorption that overcome some of the procedural problems with the Schilling test. Moreover, the invention also provides methods for determining whether a person has malabsorption of B12 that uses such limited amounts of radiolabeled B12 that in some embodiments, the body samples taken for measurement do not qualify as radioactive waste under U.S. regulations, markedly easing the handling and paperwork requirements for conducting the test. The methods of the invention therefore overcome some of the problems that have reduced recent use of the Schilling test, and are expected to result in improved monitoring of the B12 absorption of the at-risk population, thereby improving the public health.

A further advantage of the invention is that $^{14}C$ has a half life of thousands of years, while $^{60}Co$ has a half life of 5.26 years and $^{57}Co$, which is currently the most commonly used isotope, has a half life of 270 days. Thus, cobalt-labeled B12 has a relatively short shelf life and cannot be maintained for substantial periods, while the half life of $^{14}C$-labeled B12 is so long that it can be considered as stable for the uses contemplated herein.

A. Controlled C and H Labeling of B12

"Vitamin B12" or "B12" refers to a "family of substances composed of tetrapyrrole rings surrounding a central cobalt atom with nucleotide side chains attached to the cobalt. The overall group name is cobalamin, with each of the different cobalt-linked upper axial ligands conferring a different name: methyl (methylcobalamin), hydroxyl (hydrocobalamin) $H_2O$ (aquacobalamin), cyanide (cyanocobalamin) and 5-deoxyadenosine (deoxyadenosylcobalamin)." Klee, G., Clin. Chem. 46(8B):1277-1283 (2000) at page 1277. The current recommended international nomenclature is that the term "B12" refers to cyanocobalamin. Cyanocobalamin is not a natural version of the vitamin; rather, it is a synthetic form made by reacting other forms of cobalamin with cyanide. The reaction changes them to cyanocobalamin, and stabilizes them. It is the form of the vitamin commonly found in dietary supplements, such as multivitamins.

In a first embodiment, the invention provides methods for producing B12 (cobalamin, or "Cbl") labeled with $^{14}C$ or tritium in a manner useful for determining B12 absorption, without creating amounts of radiolabeled waste that are large in proportion to the amount of labeled B12. The methods can also be used to label the B12 with $^{13}C$-, which can be used, for example, for analysis of B12 metabolism by nuclear magnetic resonance (NMR).

As noted in the Background section, $^{14}C$ labeled cyanocobalamin (a form of B12 stabilized with cyanide) was made in 1951. See Boxer et al., supra. The labeling, however, was on the cyano group, which is labile and is cleaved off in the body. Cobalamin labeled using this method therefore dissociates from the cyanide group before the B12 is eliminated in the urine, and cannot be used in absorption studies based on urine analysis. For example, it cannot be used in place of $^{60}$cobalt- or $^{57}$cobalt-labeled cobalamin in the Schilling test.

Cobalamin can be labeled with $^{14}$C- or tritium by growing B12-producing bacteria on media radiolabeled with a variety of radiolabeled precursors and then separating out the B12 by standard techniques. But this method has several disadvantages. The label is promiscuously distributed into a multitude of molecules. Since B12 constitutes only a small proportion of the metabolic product of most microorganisms, this method yields a very small amount of labeled B12 and a much larger amount of radiolabeled waste. To compensate for this inefficiency, large fermentation or growth vessels would need to be used to realize a useful quantity of labeled B12. For example, Brown and Shemin (J. Biol Chem, 248(23):8015-8021 (1973)) synthesized $^{14}$C B12 in *Propionibacterium shermanii* grown in a medium containing L-[methyl-$^{14}$C]-methionine. The total volume of the culture medium was 9 liters with the specific activity of 10 µCi/mmole.

The methods of the present invention solve these problems. They permit providing B12 labeled in a manner useful for testing for malabsorption of B12, without creating relatively large amounts of labeled waste products. As noted, the method of Brown and Shemin resulted in specific activity of 10 µCi/mmole. By contrast, the methods described herein provide a specific activity equivalent to 40,000 to 60,000 µCi/mmole. As a result, even a microscale incubation in 0.1-0.5 L flasks can provide greater total radioactive yields of $^{14}$C- or tritiated-B12 than less efficient labeling techniques that are orders of magnitude greater in volume. The method herein also permit efficient synthesis of $^{13}$C-labeled B12.

The methods of the invention can achieve at least 10% incorporation of the label, e.g., $^{14}$C, $^{13}$C, tritium, or deuterium into a vitamin B12 composition. Often, at least 20-40% incorporation is achieved and frequently the method achieves at least 50% or 60% incorporation of the label. Typical levels of incorporation of the label into vitamin B12 is at least 70% or greater, often 90% incorporation or greater. Accordingly, the invention also provides labeled B12 compositions that have a high specific activity, for example, with respect to $^{14}$C-labeled compounds, a specific activity of at least about 5 to about 10 Ci/mol, typically greater than about 20 Ci/mol or about 30 Ci/mol, and often greater than about 40 to about 60 Ci/mol. The specific activity of tritium-labeled B12 of the invention is typically between about 1480 to about 5000 Ci/mol.

Vitamin B12 compositions in accordance with the invention comprise multiple vitamin B12 molecules. As used herein, the percent incorporation of a label refers to the average number of labeled B12 molecules in a B12 composition. For example, 100% incorporation refers to a B12 compositions that is labeled, on average, with at least one heavy atom, e.g., $^{14}$C, tritium, deuterium, or $^{13}$C, per molecule at a particular site. As appreciated by one of skill in the art, multiple sites can also be substituted with a heavy atom. In some embodiments, incorporation is at least 10%, typically at least 30%, 40%, or 50-70% incorporation. Preferably, incorporation is greater than 70%, e.g., 80%, 90%, 95% or about 100%. The percent incorporation can be determined by known methods, e.g., mass spectrometry or NMR. Percent incorporation can alternatively be expressed as the average number of molecules labeled at a particular site. For example, 80% incorporation can be expressed as an average of 0.8 atoms of label per B12 molecule in a B12 composition in which there is one heavy atom labeling site.

The methods involve exploiting the metabolic pathways of organisms that have the eut operon and which use dimethylbenzimidazole ("DMB") as the lower ligand of B12. The eut operon is well known in the art and is conserved in many bacteria. In *Salmonella enterica* serovar *Typhimurium* LT2 and other *Salmonella* spp. it includes 17 genes that are expressed only in the presence of ethanolamine plus B12. See, e.g., Kofoid, et al., J Bacteriol 181:5317-29 (1999). The operon has been carefully studied, particularly in *S. enterica* serovar *Typhimurium*. See, e.g., Roof and Roth, J Bacteriol 174:6634-6643 (1992), Roof and Roth, J Bacteriol 170:3855-3863 (1988), Roof and Roth, J Bacteriol 171:3316-3323 (1989), Sheppard and Roth, J Bacteriol 176:1287-96 (1994). The present inventors have previously elucidated and published the functions of various proteins encoded by genes in the eut operon. The discussion below will note portions of this information that are useful in understanding the present invention.

Preferably, the bacteria are facultative anaerobes, such as members of the family *Enterobacteriaceae*. In preferred embodiments, the facultative anaerobe is a *Salmonella* species. In some preferred embodiments, the facultative anaerobe is *Salmonella enterica*.

Adenosyl-cobalamin (Ado-B12, molecular weight 1570 Daltons) is a cofactor for several enzymes in *Salmonella* species, such as *S. enterica*. In *Salmonella*, the cofactor is synthesized only in the absence of oxygen, and functions in methionine synthesis and in two degradative pathways, the degradation of propanediol and the degradation of ethanolamine. Ethanolamine is degraded to acetaldehyde by a B12-dependent enzyme, and the acetaldehyde is then added to CoA to form acetyl-CoA. This pathway utilizes the products of the eut operon.

As shown in FIG. 1, cofactor B12 includes a corrinoid ring with a central cobalt atom; the molecule includes an upper ligand ("R" in FIG. 1 where "R" is an adenosyl group) covalently attached to the central cobalt by the 5' carbon of ribose. The lower B12 ligand is coordinated with cobalt and covalently attached to the ring by a nucleotide loop. A variety of lower ligands are used in different bacteria: purine, pyrimidines, and dimethylbenzimidazole ("DMB"). When *Salmonella* grows aerobically and is provided with the B12 precursor cobinamide, it adds DMB as the lower ligand. The *Salmonella* genome includes at least three genes that can add an adenosyl group to cobalamin to form Ado-B12, the cofactor needed for ethanolamine use. The eutT gene encodes an ATP:cobalamin adenyl transferase. The gene was identified and its protein shown to produce Ado-B12 for both metabolism of ethanolamine and continued induction of the eut operon.

In particular, the methods of the invention exploit the discovery that a strain of *S. enterica* serovar *Typhimurium* LT2, TT24,733 (genotype: cbiD24::MudJ), cannot grow in aerobic conditions when ethanolamine as the only carbon source without the presence of both cobinamide ("Cbi," a B12 precursor lacking the lower ligand. Cbi is usually given as dicyanocobinamide) and DMB, yet the strain retains the other relevant enzymes, allowing the strain to use exogenously supplied cobinamide and DMB to make B12. The *Salmonella* bacteria were grown aerobically on ethanolamine is the sole carbon source. Thus, they must form cofactor Ado-B12 from the DMB and cobinamide so that they may metabolize the ethanolamine to grow. As noted above, this requires the presence of the cofactor Ado-B12. *Salmonella* cannot synthesize B12 de novo under aerobic conditions. Further, they cannot grow aerobically on ethanolamine when solely cobinamide is provided. Growth of these organisms can be restored, however, by adding DMB. Thus, bacteria on an ethanolamine media in aerobic conditions and provided with $^{13}$C-, $^{14}$C-, deuterium or tritium labeled DMB and cobinamide will take up the labeled DMB and cobinamide so that they can metabolize the ethanolamine. Persons of skill will recognize that, conversely, bacteria on an ethanolamine media in aerobic conditions and provided with $^{13}$C-, $^{14}$C-, deuterium, or tritium labeled cobinamide and DMB will take up the labeled cobinamide and DMB so that they can metabolize the ethanolamine. Alternatively, both the cobinamide and the DMB can be labeled.

Use of the mutant strain is not necessary for the practice of the invention, but is preferred since it removes the concern that localized anaerobic conditions might form in the medium that might permit the organism to synthesize unlabeled B12 through the normal pathway. This increases the specific activity of the resulting B12. Use of non-mutant strains is also expected to result in B12 with sufficient specific activity to be used in absorption assays. As noted, however, non-mutant strains may also produce some unlabeled B12 in pockets of anaerobic conditions in the media, which may modestly dilute the labeled B12 with unlabeled B12. With *S. enterica Typhimurium*, this possibility can be reduced by not providing an alternate electron acceptor, such as tetrathionate, in the grown medium.

In the studies underlying the present invention, the DMB was labeled with $^{14}$C specifically in the carbon of the small benzimidazole ring, C-2. Conveniently, this can be done by acquiring a precursor of DMB, dimethylphenylenediamine (Sigma, St. Louis, Mo.) and inserting a $^{13}$C or $^{14}$C carbon from formic acid. Formic acid, sodium salt [$^{14}$C] is commercially available, for example, from Moravek Biochemicals, Brea, Calif. Any carbons or hydrogens in DMB can be labeled instead, however, so long as the DMB as a molecular entity is labeled. Alternatively, the Cbi can be labeled, instead of the DMB, or both can be labeled. The labeled molecule can then be recovered by standard techniques, such as those described in Florent J. and Ninet, L. Vitamin B12. In: Microbial Technology, 2nd ed. Peppler J H, Perlman D, eds. New York: Academic Press, 1979.

The procedure followed is not a normal pathway in B12 synthesis. Advantageously, the method bypasses the normal feedback mechanisms controlling bacterial B12 synthesis and results in the production of about 1000 times more B12 than the bacteria would produce under normal conditions by avoiding the feedback steps that would normally limit output. Further advantageously, it has been found that the method of the invention provides B12 in which a high percentage of the B12 produced is labeled at only one carbon. B12 labeled at only one carbon is advantageous because it provides reproducible material that is largely unaffected by modest changes in growth conditions, as well as the labeling necessary to conduct absorption assays.

Labeling with $^{14}$C or tritium is also advantageous as it avoids exposing patients and staff to the gamma radiation emitted by radioactive cobalt and, when accelerator mass spectroscopy ("AMS") is used, as discussed below, permits "microdosing" and sharply reduces the radioactivity necessary to accomplish the absorption studies. Thus, its use facilitates acquiring regulatory approval. Although the studies were conducted using $^{14}$C, and $^{14}$C is particularly preferred it is understood that the studies could have been conducted with $^{13}$C- or deuterium or tritium-labeled B12. Tritium is particularly useful for AMS analysis.

It is believed that other facultative anaerobic organisms with functional eut_operons can be substituted for *S. enterica* in the methods of the invention. Lawrence and Roth (*Evolution of coenzyme B12 synthesis among enteric bacteria: evidence for loss and reacquisition of a multigene complex.* Genetics. January; 142(1): 11-24 (1996)) have reported more than 120 strains that are capable of utilizing ethanolamine as a carbon source. The eutBC genes from *Salmonella enterica* serovar *Typhimurium* LT2 encode the vitamin B12-dependent ethanolamine ammonia lyase. This is the core enzyme involved in ethanolamine metabolism. Analysis of NCBI database by BLASTP search algorithm reveals that many organisms contain protein homologs to EutB from *Salmonella enterica* serovar *Typhimurium* LT2. The following species contain EutB homologs (protein identities greater than 45%) and are expected to work in the methods of the invention: *Listeria monocytogenes, Symbiobacterium thermophilum, Fusobacterium nucleatum, Desulfitobacteriumi hafniense, Burkholderia fungorum, Burkholderia cepacia* (Proteobacteria), *Burkholderia pseudomallei, Chromobacterium violaceum, Ralstonia solanacearum, Cytophaga hutchinsonii, Rubrivivax gelatinosus, Pseudomonas putida, Ralstonia metallidurans, Pseudomonas fluorescens, Pseudomonas syringae, Magnetospirillum magnetotacticum, Pseudomonas aeruginosa, Xanthomonas axonopodis, Azotobacter vinelandii, Streptomyces avermitilis, Xanthomonas campestris, Rhodopseudomonas palustris, Rhodospirillum rubrum, Bradyrhizobium japonicum, Agrobacterium rhizogenes, Rhodococcus erythropolis, Ralstonia eutropha, Enterococcus faecalis, Photorhabdus luminescens.*

*Salmonella* spp, *Escherichia* spp, *Klebsiella* spp and *Citrobacter* spp. with functional eut_operons are preferred for use in the methods. Whether or not any particular organism can be used in the methods of the invention can be tested by routine assays, such as the exemplar assay set forth in the Examples.

As noted above, many of these organisms can also grow on propandiol under aerobic conditions. On propandiol, the organisms synthesize a co-factor that is slightly different than B12, that uses an adenine in place of DMB. Thus, this pathway requires Cbi, but not DMB. The different co-factor is known as "pseudo-B12," and is not useful in humans. When the organisms are grown on propandiol in the presence of Cbi, but not DMB, therefore they make pseudo-B12 rather than B12. When given propandiol, Cbi, and DMB, the organisms switch off the pseudo-B12 pathway and make B12. Thus, the organisms can be grown on propandiol in place of ethanolamine to produce labeled B12. To avoid contamination of the B12 with pseudo-B12, however, growth on ethanolamine is preferred.

B. Assays Using $^{14}$C-, $^{13}$C- or $^3$H-Labeled B12 in Place of $^{60}$Co-Labeled B12

In one set of embodiments, $^{14}$C- or tritium labeled cobalamin produced by the methods of the invention can be used to replace cobalamin labeled with radioactive isotopes of cobalt, such as $^{60}$Co, in the Schilling test. In these embodiments, the test is a conducted by using $^{14}$C- or tritium-labeled cobalamin, having the patient collect a complete 24 hour urine sample, and determining the percentage of absorption of the labeled cobalamin, as is done in the classic Schilling test using cobalamin with radioactively labeled cobalt. Advantageously, since the $^{14}$C or tritium emits only weak beta particles, unlike radioactive cobalt, which emits both beta particles and strong gamma radiation, neither the medical staff nor the patient is exposed to gamma radiation.

The classic Schilling test measures radioactivity in the urine, typically by use of a scintillation counter. Because the radioactive isotope of cobalt has a different atomic mass than does the non-radioactive cobalt normally present in the body, the amount of radioactive cobalt present can also be determined by mass spectroscopy. This method can also be used to determine the amount of $^{14}$C- or tritium labeled cobalamin produced by the methods of the invention. $^{13}$C-labeled B12 is non-radioactive, but does have a mass difference which can be exploited by using mass spectroscopy to determine the amount of B12 present. This of course further reduces the exposure of medical personnel and patients to radiation and is a particular advantage of this form.

C. Microdose Assays Using $^{14}$C- or Tritium-Labeled B12

In a further set of embodiments, $^{14}$C- or tritium-labeled cobalamin produced by the methods of the invention can be used in assays which lower the amount of radioactive material used to levels so low that they are not considered radioactive under current Federal regulations. These embodiments exploit the properties of Accelerator Mass Spectroscopy, or "AMS". AMS is described in more detail in a succeeding section, but it is considered capable of detecting and quantifying $^{14}$C or tritium to attomole concentrations. Accordingly, it requires much smaller sample volumes. Unfortunately, radioactive cobalt cannot be used in AMS methods, and therefore, unlike $^{14}$C-B12 or tritiated-B12, cobalt-labeled B12 cannot be used to microdose patients for AMS testing.

The AMS procedure can be used on urine samples, as used in the Schilling test. Desirably, however, the procedure is used on blood samples, which because of the sensitivity of the assay, can be quite small in volume. Further, because the assay can be performed on blood samples, there is no need to follow the first administration of B12 with an excess of B12 to flush the labeled dose into the urine, as is done in step two of the Schilling test. Thus, if the level of absorbed B12 is low, further studies equivalent to later stages of the Schilling test can be performed without waiting weeks for the subject to eliminate the excess B12. Eliminating this waiting period improves patient compliance and, by reducing the period before the patient starts B12 supplementation if it is needed, is safer for the patient.

In the assays, $^{14}$C-labeled cobalamin or tritiated B12 is administered orally to the subject. Any labeled cobalamin not absorbed by the subject will be excreted in the stool, and of course only the absorbed cobalamin will be represented in the blood. Absorption levels of B12 in normal individuals and in those with pernicious anemia can be readily determined by measuring such levels in cohorts of individuals as set forth in the Examples. The level in the subject at the time of measurement ($T_M$) is then compared to the levels of absorption at the equivalent time in the cohorts studied to determine if the subject's absorption of B12 is normal or warrants further testing.

II. Vitamin B12

A. Chemical Structure and Variants

Vitamin B12 is a generic descriptor for all corrinoids (cobalt-containing compounds) exhibiting the biological activity of cyanocobalamin. "Cobalamin" is the general term used to describe a group of corrinoids that have a particular structure that contains the sugar ribose, phosphate, and the base 5,6-dimethylbenzimidazole ("DMB") attached to a corrin ring. Cobalamins have three parts, as indicated by FIG. 1: a planar corrin ring which contains four ligands for the central cobalt atom, a lower (alpha) ligand donated by the DMB nucelotide, and an upper (beta) ligand, designated in the Figure by the "R" group).

The axial alpha ligand can be one of three groups: a benzimidazole, a purine, or a phenolic compound. Only DMB in this position is biologically active in humans, and when this base is absent, the compound is called a cobamide or a cobinamide.

The axial beta ligand of vitamin B12 is often said to be a cyano group, as this is the form of the vitamin that is most often found in supplements. However, this compound, cyanocobalamin, is not found in nature. Coenzymatic forms of the vitamin have either a methyl or deoxyadenosyl beta ligand, and other naturally-occurring forms of the vitamin include those with hydroxo- and aqua-beta ligands.

Cyanocobalamin [CAS registry Number 68-19-9] has an empirical formula of $C_{63}H_{88}N_{14}O_{14}PCo$ and a molecular weight of 1355. It forms red, needlelike crystals, and is soluble in water (1.2% at 25° C.), alcohol, and phenol, but is insoluble in acetone, chloroform and ether. Crystallization is often performed from water-acetone solutions, from which it forms red, needlelike, hygroscopic crystals. Cyanocobalamin is heat stable and it has a melting point above 300° C. Cyanocobalamin has three absorption maxima with the following extinction coefficients: $\epsilon_{278}=16300$; $\epsilon_{361}=28100$; $\epsilon_{550}=8700$.

Cyanocobalamin ("CNCbl") is relatively stable compared to the other cobalamin ("Cbl") compounds hydroxocobalamin ("HOCbl"), adenosylcobalamin ("Ado-Cbl"), and methylcobalamin ("MeCbl"). These less stable forms, however, are readily converted to cyanocobalamin upon treatment with cyanide, as the cyanide group has the highest affinity for cobalt amongst the known β-ligands. Since B12 occurs in such low concentrations, even trace amounts of cyanide will convert all of the corrinoids into their cyanide forms.7

Mild acid hydrolysis of cyanocobalamin induces the removal of the nucleotide, while treating alkaline cyanocobalamin solution with cyanide yields dicyanocobalamin, an unstable, biologically inactive compound with cyanide groups in both the alpha and beta ligand positions. The cyanidation of all α-substituted cobalamin compounds requires light because the photolytic cleavage of the α-group is necessary before the substitution of the cyanide group can occur.

Due to the lengthy (>70 steps) chemical synthesis, vitamin B12 for supplements is generally produced biosynthetically from large-scale bacterial fermentations. Bacteria produce vitamin B12 compounds with several different R (beta) substituents including methyl-, 5'-deoxyadenosyl-, hydroxo- and aqua-groups. However, these cobalamins are converted to the more stable cyanocobalamin, with the cyano R-group resulting from the extraction procedure by which the compound is isolated from bacterial cultures. Cyanocobalamin is therefore the form that is most often found in supplements and, is easily converted in humans to one of the biologically active forms of the vitamin.

B. Bacterial Use and Synthesis

Organisms that are used for the commercial production of B12 for supplements include *Streptomyces griseus, Streptomyces aureofaciens, Propionibacterium shermanii, Propionibacterium acidipropionici* and *Pseudomonas denitrificans. P. denitrificans* is used almost exclusively in industrial processes and genetic alterations of the bacteria have increased the yield of the vitamin to as much as 300 mg per liter of bacterial growth.

In bacteria, AdoCbl participates as a coenzyme for several enzymes, all of which have in common a hydrogen atom migrating from one carbon atom of the substrate to a vicinal carbon in exchange for a group X. In almost every enteric bacteria, coenzyme B12 is essential for the anaerobic fermentation of 1,2-propanediol, ethanolamine, and glycerol. In some bacteria, the subsequently generated propionaldehyde and the acetaldehyde serve as carbon and energy sources via oxidation to propionyl-CoA and acetyl-CoA, respectively.

Diol dehydratase or propanediol hydro-lase (EC 4.2.1.28) converts 1,2-propanediol and other 1,2-diols to propanaldehyde and the corresponding aldehydes in the presence of AdoCbl. It also converts glycerol to β-hydroxypropionaldehyde. Diol dehydratase plays an essential metabolic role in producing aldehyde, which serves as both an intermediate and an electron acceptor in the fermentation of 1,2-diols.

Dependent upon AdoCbl, this enzymatic reaction has been widely used to study the mechanism of AdoCbl.

Glycerol dehydratase (dependent upon AdoCbl) or glycerol hydro-lase (EC 4.2.1.30) also catalyzes the conversion of glycerol to α-hydroxypropionaldehyde, which is further reduced to 1,3-propanediol. The enzyme is also responsible for catalyzing 1,2-diols to the corresponding aldehyde. This reaction balances the reducing equivalents generated by glycerol dehydrogenase. Glycerol dehydratase is common in enterics but is absent from Salmonella and E. coli.

Ethanolamine ammonia lyase (EC 4.3.1.7) converts ethanolamine to acetaldehyde and ammonia. Ethanolamine is encountered frequently in nature as part of common lipids, phosphatidyl ethanolamine, and phosphatidyl choline. Glycerol dehydratase (dependent upon AdoCbl) or glycerol hydro-lase (EC 4.2.1.30) also catalyzes the conversion of glycerol to β-hydroxypropionaldehyde, which is further reduced to 1,3-propanediol.47,60-63 The enzyme is also responsible for catalyzing 1,2-diols to the corresponding aldehyde.58 This reaction balances the reducing equivalents generated by glycerol dehydrogenase. Glycerol dehydratase is common in enterics but is absent from Salmonella and E. coli. 47,60-62

Ethanolamine ammonia lyase (EC 4.3.1.7) converts ethanolamine to acetaldehyde and ammonia.58 Ethanolamine is encountered frequently in nature as part of common lipids, phosphatidyl ethanolamine, and phosphatidyl choline.

There are at least 21 genes involved in cobalamin synthesis in bacteria and the process probably requires 20-30 different enzymatic steps. Biosynthesis of the corrin moiety and of the nucleoside component proceed separately from each other, then are united. The synthesis is complex and will not be recounted in detail herein.

III. Use of Accelerator Mass Spectrometry (AMS) to Assess B12 Absorption and Kinetics.

An Accelerator Mass Spectrometer is a type of tandem isotope ratio mass spectrometer that measures the ratios of isotopes to parts per quadrillion. For example, it can measure down to as few as $10^5$ atoms of $^{14}C$. In AMS, negative ions are generated in a cesium ion source and accelerated by a potential of 0.5-10 million volts. The accelerated ions are smashed through a thin carbon foil or inert gas that removes electrons and destroys all molecular species. After passing through a high-energy mass spectrometer and various filters, carbon nuclides are measured with current and particle detectors. AMS services are available for a fee through national laboratories such as Lawrence Livermore, or through a growing number of commercial entities.

In the past, AMS was applied to geochronology, but has more recently been developed for bioanalytical tracing (Vogel, J. S. et al., Analytical Chemistry 67:A353-9 (1995)). Its advantages over non-isotopic and stable isotope labeling methods have been recently reviewed (Vogel, J. S. et al., In: Mathematical Modeling in Experimental Nutrition. Clifford A J, Muller H-G, eds. New York: Plenum (1998)). AMS detects $^{14}C$ concentrations to parts per quadrillion, quantifying labeled biochemicals to attomole levels in milligram-sized samples and achieving an increase in sensitivity of $10^{5-6}$ over traditional liquid scintillation counting ("LSC"). LSC, of course, relies on counting particles emitted by decaying atoms, whereas AMS quantitates the atoms themselves by their mass. AMS can use a smaller sample since it does not quantify upon only the small percentage of atoms that may be decaying at any one point in time.

Because AMS is a combustive process, biological fluids and tissues can be analyzed directly without cleanup, fractionation or derivatization. Using this approach, nutrient mass-balance studies are facile and quantitative with very minimal radiation risk to the subject.

As noted, AMS allows for the detection and quantification of $^{14}C$-labeled substrates at the attomole ($10^{-18}$) level. This level of sensitivity, which far exceeds the limits of conventional liquid scintillation counters, makes AMS uniquely suited for assessing the intestinal absorption of $^{14}C$-labeled substances after oral ingestion. Since only a small percentage of atoms in a sample are decaying over the relatively small time the sample is being counted in an LSC, a sample measured by LSC must be large enough for the number of atomic decays to be reliably measured. Unlike LSC, AMS directly counts the $^{14}C$ nuclide without regard for its rate of decay. As a result, it is approximately one million-fold more sensitive than LSC. Furthermore, AMS is typically carried out on samples containing only 1 mg of carbon, thus permitting analysis from microliter-sized biological samples. Importantly, absorbed radioactivity can be easily detected in biological fluids even when a small amount of substrate with low specific activity is ingested. This allows for absorption studies to be carried out with minimal or insignificant exposure of the test subject to the radioactive substrate.

As an example, AMS has been exploited to detect $^{14}C$-labeled folic acid in the blood and urine after a physiological (100 nanoCi; 35 µg) oral dose (Clifford, A. J. et al., In: Advances in Experimental Medicine and Biology. Clifford A J, Muller H-G, eds. New York: Plenum (1998)). Signal is detectable for greater than 6 months in red blood cells. Importantly, the extreme sensitivity of AMS has significantly reduced the size of the radiation dose for human studies to levels that are often considered non-radioactive; the Consolidated Federal Register (CFR) defines radioactive waste as materials containing 50 nanoCi per gram (10 C.F.R. §20.2005). In a $^{14}C$-folic acid study, 100 nanoCi total $^{14}C$ was sufficient to perform detailed kinetic experiments in a 90 kg human for greater than 9 months (Clifford, A. J. et al., In: Advances in Experimental Medicine and Biology. Clifford A J, Muller H-G, eds. New York: Plenum (1998)). Under the assumption of total body dispersal (V distribution=42 liters), the biological samples and generated laboratory waste are legally classified as "nonradioactive" according to 10 C.F.R. §20.2005. Moreover, the total effective radiation dose equivalent associated with 100 nanoCi $^{14}C$-folic acid is 1.1 mrem; in contrast, the total effective dose equivalent of a typical chest X-ray is 23 mrem and that of a 2 h commercial airliner ride is 1.1 mrem. Therefore, AMS can be safely exploited to assess B12 absorption and kinetics. The requirement for AMS analysis is that the sample contain approximately 1 mg of carbon. Relatively small aliquots of human biological samples contain sufficient carbon content for reliable measurements. AMS testing for B12 will be performed on blood samples on the order of several milliliters, obtained by fingerstick.

IV. Use of Labeled B12 for Metabolic Studies

A number of medical disorders relate to abnormal B12 metabolism. For example, there are disorders related to the transcobalamins that serve as the intestinal and blood transport proteins for B12, and disorders in which the body cannot convert cyanocobalamin to the physiologically active form of the vitamin. Studies of these disorders have been hindered by the fact that the only labeled B12 with adequate specific activity has been $^{57}Co$, which not only emits gamma radiation, but also decays into to a non-physiologically active form. The availability of C- and H-labeled forms of the vitamin makes possible a range of studies, such as plasma clearance, turnover rate, enzyme kinetic measurements, and studies of the uptake and distribution of the vitamin, which will enhance the ability to diagnosis and monitor these conditions.

The invention also provide physiologically acceptable compositions comprising labeled B12 of the invention. A "physiologically acceptable composition" refers to a composition that is appropriate for administration to a subject. Such physiological compositions comprise the radio-labeled vitamin B12 and a physiologically acceptable carrier, e.g., water, or another pharmaceutically acceptable carrier or diluent.

EXAMPLES

Example 1

This Example describes the synthesis of $^{14}$C-dimethylbenzimidazole.

(a) Chemical Synthesis.

Synthesis of the $^{14}$C-dimethylbenzimidazole was performed using a procedure modified from Phillips. (Phillips, M. A. J Chem Soc, page 2393 (1928)). Formic acid, sodium salt [$^{14}$C] in ethanol, 1 mCi (0.0182 mmoles; Moravek Biochemicals; Brea, Calif.), was placed into a 10 mL boiling flask and 500 μL phosphate buffer at (pH 7.4, 100 mM) was added. The ethanol and water solvents were evaporated to dryness using a rotary evaporator under reduced pressure. The residue was resuspended in 1 mL of 4N HCl and 111 μmoles o-dimethylphenylenediamine was added. The flask was placed in a sandbath and equipped with a water-chilled condenser. The reaction was heated to reflux for 2 hours. The flask was allowed to cool to room temperature and the contents neutralized with concentrated aqueous ammonia to pH 7.

(b) Solid-Phase Extraction (SPE).

SPE cartridges (5 g bond Elut C18, Varian; Palo Alto, Calif.) were prepared for use per the manufacturer's instructions. Samples were loaded onto the cartridges, then the cartridges were washed with 2 column-volumes of water. The DMB was eluted with 3 mL methanol, the eluent evaporated to dryness, then resuspended in ethanol.

(c) Purification of $^{14}$C-DMB by HPLC.

Purification was performed with a Hewlett Packard series 1100 HPLC equipped with an automatic injector, quaternary pump, diode array detector, and Chem Station software. The instrument was fitted with an Adsorbosphere HS C18 (3 μm; 150 mm×4.6 mm) column (Alltech; Deerfield, Ill.) and a Brownlee Newguard RP-18 precolumn (Alltech; Deerfield, Ill.). The mobile phases were prepared using HPLC grade solvents from Fisher. The ternary solvent system was 34.2% water, 33.8% methanol, 32% acetonitrile (with +0.02% w/vol ammonium acetate). The flow rate was held constant at 0.800 mL/min. A standard of DMB had a retention time ($t_r$) of 7.3 min. The sample obtained from the synthesis (post-SPE cartridge) was isolated in multiple injections on the chromatographic system and the eluent fraction corresponding to DMB standard was collected and pooled for each run. The pooled fractions were evaporated to dryness under reduced pressure, resuspended in absolute ethanol, and an aliquot counted by liquid scintillation counting (LSC).

Example 2

This Example sets forth and discusses the results of the synthesis set forth in the previous Example.

A small aliquot of sample was injected into the HPLC and 30-second fractions were collected and analyzed for $^{14}$C by LSC. The resulting $^{14}$C counts (in disintegrations per minute) were co-plotted with the UV/vis absorbance of the chromatogram over time.

The entire product was run in multiple injections through the HPLC and the peak in each run corresponding to the DMB was collected and pooled. The collection was evaporated to dryness and the resulting 0.35 mCi $^{14}$C-DMB was resuspended in ethanol for future use in labeling experiments with the bacteria. The total yield of purified $^{14}$C-DMB was 0.35 mCi or 35%.

The yield from the $^{14}$C-DMB synthesis was only 35% of the theoretical yield. One possible explanation for the low yield is that some DMB stuck to the SPE column and was never eluted. To test this possibility, 3.4 nCi of $^{14}$C-DMB was loaded onto an SPE column using the method described in 5.2.1(b). After elution with methanol (per the method), there were no radioactive counts in the collected eluent. The SPE packing material was removed from the cartridge and counted by LSC and all 3.4 nCi were found to have remained adhered to the stationary phase. Thus, the $^{14}$C-DMB had a high affinity for the C18 SPE stationary phase. The $^{14}$C-DMB that was recovered is assumed to have been due to the excessive amount of DMB loaded onto the column that exceeded the capacity of the C18 phase in the SPE cartridge.

Despite the low yield due to loss in the SPE cartridge, the $^{14}$C-DMB that was produced was of very high chemical and isotopic purity. The coelution of the DMB absorption peak with the $^{14}$C-radioactivity peak and the absence of additional rises in $^{14}$C activity elsewhere in the radiochromatogram suggested the reaction product to be $^{14}$C-DMB of high purity. The radio-peak was collected and pooled from multiple HPLC runs and used as the active precursor for bacterial vitamin $B_{12}$ biosynthesis.

Example 3

This Example describes the production of $^{14}$C-labeled B12 in *Salmonella enterica*. The strain used was a derivative of *Salmonella enterica* serovar *Typhimurium* strain LT2, strain TT24733, genotype cbiD24::MudJ (John Roth, U C Davis).

(a) Labeling Medium. Labeling medium consisted of no citrate E (NCE) medium (Davis, R., Botstein, D., Roth, J., Advanced Bacterial Genetics. Cold Spring Harbour Laboratory, New York (1980)), supplemented with sterile solutions of: glycerol (Mallinckrodt; Phillipsburg, N.J.) to give a final concentration of 5 mM, ethanolamine hydrochloride (Sigma; St.Louis, Mo.) to give a final concentration of 40 mM, and dicyanocobinamide (Sigma; St.Louis, Mo.) to give a final concentration of 250 nM. Approximately 130 mL of labeling medium was added to a sterile 500 mL conical flask and $^{14}$C-DMB was added.

Inoculum was prepared by streaking the *S. typhimurium* serovar *Typhimurium* onto a LB plate and incubating for about 16 hours to obtain single colonies. A single colony from this plate was used to inoculate 3 mL of NCE medium supplemented with 0.2% glycerol in a sterile glass test tube (Fisher; Hampton, N H). This was covered with sterile foil and the solution was incubated for 16 hours with shaking at 37° C. Inoculation was effected by addition of 1% vol/vol of the inoculum to the labeling medium. Incubation of the organism in the labeling medium was carried out in the dark at 37° C. for 24 hours at 250 RPM.

Extraction of cyanocobalamin from cells was performed as follows. Bacterial cells were transferred to 50 mL polyethylene centrifuge tubes, then pelleted by centrifugation for 15 minutes at 6,000 g, supernatants aspirated, and cells resuspended and vortexed with 12 mL of NCE. The pellets were resuspended in 1 mL of an aqueous solution of potassium cyanide (50 mg/mL), then a further 5 mL of methanol was added. Samples were vortexed for one minute, then placed in a 60° C. water bath. After one hour, samples were vortexed for another minute, then replaced into the water bath for 12 hours.

After the overnight incubation, an additional 5 mL methanol was added to each sample and the sample vortexed for one minute. The samples were then centrifuged at 20,000 g for one hour. The supernatants, which now contain the extracted corrinoids, were removed from the pellet and evaporate to dryness. Dried samples were resuspend in 3 mL water and syringe filtered (0.22 μm) so as to remove any insoluble material.

Solid-Phase Extraction cartridges (5 g bond Elut C18, Varian, Palo Alto, Calif.) were prepared as per the manufacturer's instructions. Samples were loaded onto the cartridges, then the cartridges were rinsed with 2 column-volumes of water. The corrinoids were eluted with 3 mL methanol and the solvent evaporated to dryness.

HPLC Method a Hewlett Packard series 1100 HPLC equipped with an automatic injector, quaternary pump, diode array detector, and Chem Station software. The instrument was fitted with a Zorbax Eclipse XDB C18 (3.5 μm) analytical column (3.0 mm×15 cm) and a Brownlee Newguard RP-18 precolumn (Alltech; Deerfield, Ill.). The mobile phases were prepared using HPLC grade solvents from Fisher. Solvent A was 90/10 water/methanol and solvent B was methanol, initial conditions were 82/18 A/B which was held for 12 min; this phase was followed by a linear gradient that obtained 25/75 A/B at 16 min. These conditions were held constant from 16-19 minutes, then the system was returned to starting conditions from 19-23 minutes. The flow rate was held constant at 0.360 mL/min. The retention time of a cyanocobalamin standard was ≈7.5 minutes. Semi-purified bacterial extracts were separated using this. The peak(s) corresponding to the retention time of the cyanocobalamin standard were collected and evaporated to dryness, then resuspended in water for re-chromatography or storage at −70° C.

LC/MS utilized the same software, column, precolunm, and model HPLC as for the HPLC methods described above, but included a quadrupole HP 1100 mass spectrometer. The mobile phases were also the same, but each had an addition of 0.5% formic acid to aid in ionization. Initial conditions were 86/14 A/B which was ramped with a linear gradient to 65/35 A/B at 12 minutes. These conditions were followed by another linear gradient to 25/75 A/B at 16 min, which was held constant from 16-19 minutes. The system was returned to starting conditions from 19-23 minutes. The flow rate was held constant at 0.360 mL/min. The retention time of a cyanocobalamin standard was ≈9.1 minutes. The electrospray (positive) mass spectrometer utilized a nitrogen drying gas flow rate of 12 L/min at 350° C. The nebulizer pressure was set to 30 psi, the $V_{cap}$ to 3500V, and the fragmentor to 200V. MS data were acquired by scanning from 300-1500 m/z. The LC/MS was performed on non-radioactive samples that were grown in tandem with the $^{14}$C-labeled samples. The LC/MS was used to verify the production of cyanocobalamin in these samples, which could then be used to confirm $B_{12}$ production in the samples with the $^{14}$C-labeled precursors.

Example 4

This Example sets forth and discusses the results of the studies.

Three samples of approximately 130 mL each were grown with the labeled precursors. The mass of vitamin $B_{12}$ produced was determined using the UV data from the HPLC and this was normalized to account for the total mass of cells that each experiment produced.

To determine the radiological purity of the vitamin B12, an aliquot of each replicate was injected into the HPLC and 30-second eluant fractions were collected. Each fraction was analyzed for radioactivity by liquid scintillation counting and the radioactivity in disintegrations per minute (dpm) was plotted over time, along with the real-time absorbance of the samples at 361 nm. All three replicates produced similar results. The precise coelution of the radiation and absorbance peaks and the absence of additional rises in $^{14}$C activity elsewhere in the radiochromatogram suggested the reaction product to be $^{14}$C-cyanocobalamin of high purity.

The UV/vis spectrum from 220-650 nm can be used to confirm that the absorbance peak at 361 nm is indeed due to cyanocobalamin. The spectrum for the chromatographic peak with a retention time corresponding to vitamin $B_{12}$ from a bacterial extract was compared to a commercial standard of vitamin $B_{12}$ (Sigma; St. Louis, Mo.). The bacterial extract peak had a UV/vis spectrum characteristic of vitamin $B_{12}$, including the requisite peak maxima at 361 and 551 nm. Additionally, the ratio of absorbance of the 361 nm/551 nm of the biosynthetic product was 3.14, matching that of the cyanocobalamin standard.

An additional method used to positively identify cyanocobalamin as the reaction product is mass spectrometry. Non-labeled samples were grown and extracted in tandem with the $^{14}$C-labeled samples, and these non-labeled samples were analyzed by LC/MS.

The mass spectra showed a m/z peak at 1355.7, which indicates the CN-Cbl+ ion. There was also an m/z of 1393.7, which indicates a cyanocobalamin potassium adduct at 1393.7. As potassium cyanide is used to cyanidate the cobalamins, residual potassium would likely remain in the sample and thus the potassium adduct is expected. The mass spectrum of the cyanocobalamin standard also had the CN-Cbl+ ion at m/z=1355.6 and a potassium adduct at m/z=1394.7, however there was also a peak at m/z=1377.6. This is likely due to a sodium adduct of cyanocobalamin, which may result from a mixture of potassium cyanide and sodium cyanide being used in the synthetic process, or as an impurity in the reagent or water used in the standard preparation.

In addition to identifying cyanocobalamin as the biosynthetic product, it is also important to determine the degree of incorporation of $^{14}$C into the molecule. 'Specific activity' refers to the total amount of radioactivity per mole unit of a compound, generally expressed as mCi/mmol. The maximum value of a specific activity for a compound with 1 atom of $^{14}$C at 100% isotopic incorporation is 62.4 mCi/mmol. The vitamin B12 produced in this study is capable of having, at most, one $^{14}$C atom per molecule, as there is only one DMB moiety per molecule of cyanocobalamin. The average specific activity of the $^{14}$C-vitamin B12 produced was 47.3 mCi/mmol, indication that there were, on average, 0.758 atoms of $^{14}$C per molecule of cyanocobalamin.

The total mass of vitamin B12 produced from the three replicates was calculated, as well as the total radioactivity. The total mass yield of vitamin B12 produced was 25 μg (18.6 nmoles) and 880 nCi, corresponding to a specific activity of 47.3 mCi/mmol. The specific activities of the $^{14}$C-vitamin $B_{12}$ produced in each replication were determined and are listed in Table 1.

TABLE 1

Specific Activity of $^{14}$C-Vitamin $B_{12}$ Produced

| Sample | Total B12 (nmoles) | Total $^{14}$C (nCi) | Specific Activity | Average # $^{14}$C/molecule |
|---|---|---|---|---|
| Replicate 1 | 6.88 | 330 | 48.0 | 0.77 |
| Replicate 2 | 4.82 | 226 | 46.9 | 0.75 |
| Replicate 3 | 7.03 | 324 | 46.1 | 0.74 |

The amount of $^{14}$C desired for the vitamin $B_{12}$ dose for the human study is 100 nCi. However, the specific activity is important because the 100 nCi of $^{14}$C should not be contained in a high mass of vitamin $B_{12}$. A low mass is desired so that the normal metabolic pathways for the vitamin are not perturbed. Thus, a high specific activity of the vitamin is preferred. As the biosynthetic product has a specific activity of 47.3 mCi/mmol, a resulting 100 nCi dose of $^{14}$C-vitamin $B_{12}$ will contain 2.86 µg of the vitamin. The recommended daily intake of vitamin $B_{12}$ is 2.4 µg and a dose with a vitamin $B_{12}$ mass of less than this is desired. To remedy the discrepancy, a smaller dose can be used, as even 50 nCi is enough $^{14}$C to follow by AMS for the desired duration.

Example 5

This example describes the use of this labeled B12 and AMS to assay B12 absorption in a normal human subject. A single 1.5 µg dose of the $^{14}$C-vitamin B12 was administered orally and detected by AMS as it appeared in the bloodstream.

The subject was a healthy male aged 40 years with a body mass index (BMI) of 27.5. The subject began complete fecal and urine collection 24 h in advance of the dose and continued complete 24 h collections until Day 7. On the day of dose administration, the subject was fitted with an intravenous catheter in a forearm vein. Blood was drawn into 7 mL tubes containing EDTA. A baseline blood sample was drawn (7 AM) and the dose consumed that corresponded to 2.2 KBq of radioactivity (1.5 µg) was administered in 50 mL of drinking water in a paper cup. The volunteer was allowed to have water ad libitum thereafter, with a light meal taken 2 hr postdose. Blood samples were drawn at frequent intervals for the first 15 hr post-dose and daily thereafter. Meals were controlled for time and content on the dose administration day.

AMS analysis. Aliquots of plasma (30 µL), urine (80 µL) and a stool slurry (80 µL) were dried, combusted to CO2, and reduced to filamentous carbon using known procedures. No other processing preceded the graphization step, thus quantitative recovery was ensured. The $^{14}$C measurements were performed at the Center for Accelerator Mass Spectrometry at Lawrence Livermore National Laboratory. Measurements were conducted to <3% instrument imprecision and, in general, signal acquisition was complete to the desired statistical precision in 3-5 min per sample. The radiation exposure of the subject, due to the $^{14}$C-B12 dose, was equivalent or less than exposure due to 10 hours of intercontinental plane flight.

Figure 4:
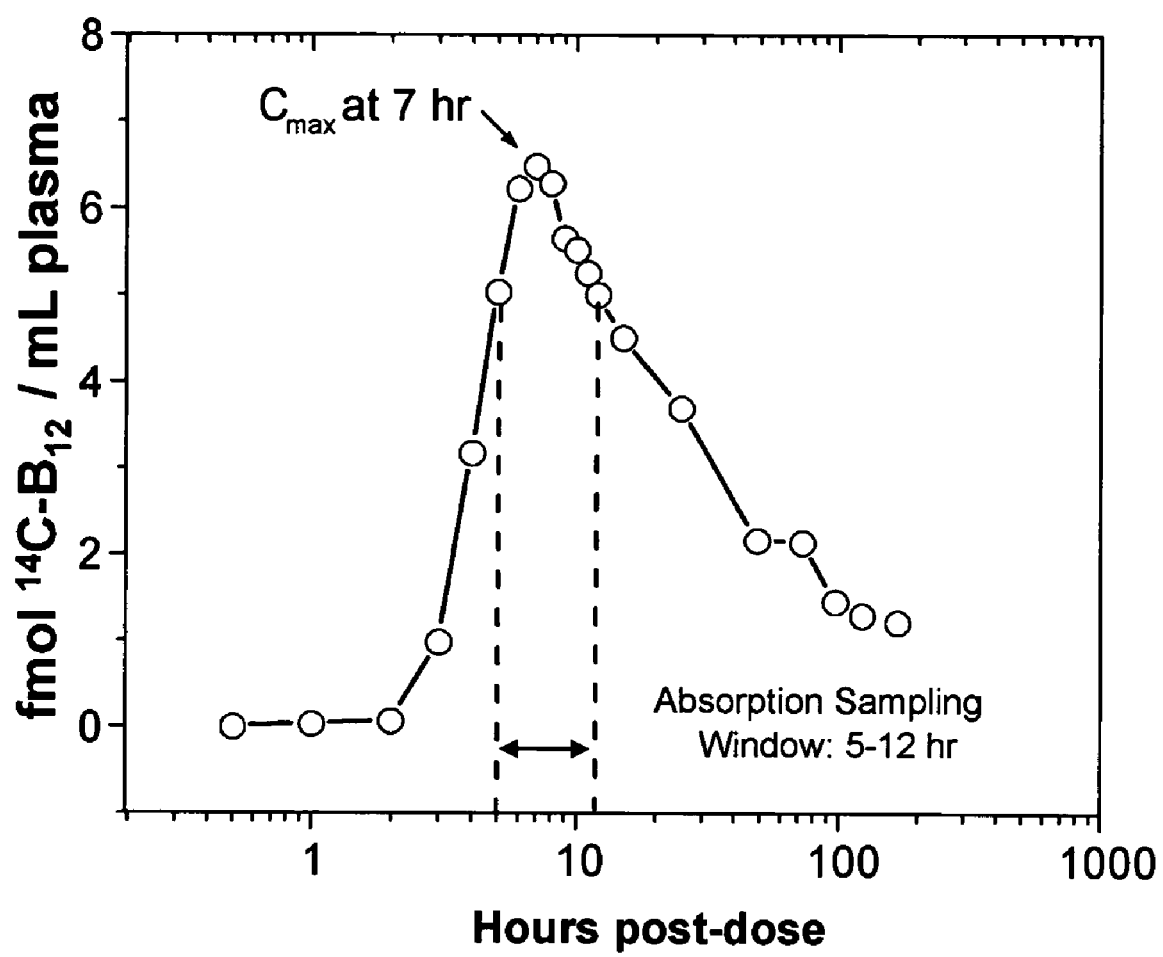
FIG. 4 shows accelerator mass spectrometry (ASM) detection of $^{14}C$ in human plasma. Units are expressed as femtomolar 14C-B12. Measurements were performed on 30 µl of plasma, the entire sample set consumed less than 1 mL of whole blood.
Figure 5:
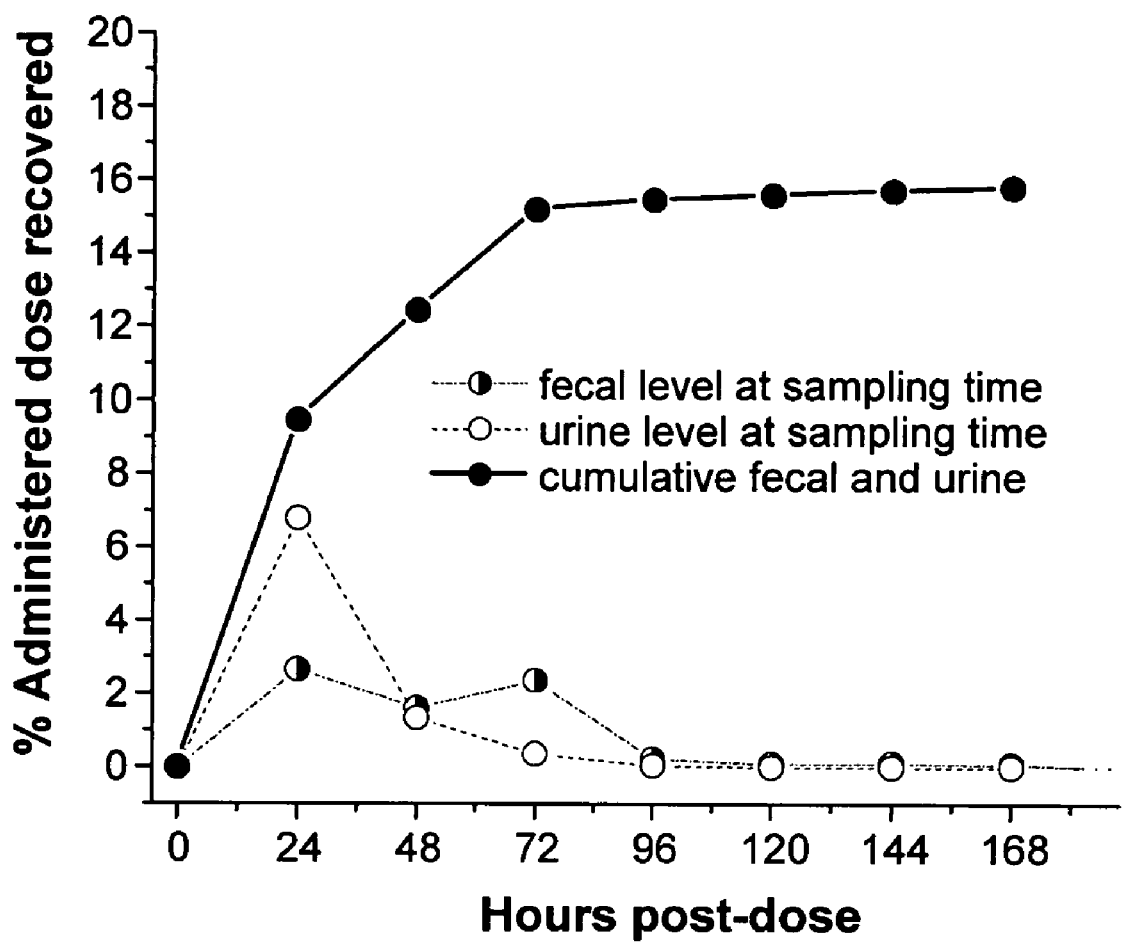
FIG. 5 shows recovery of $^{14}C$ in urine and fecal specimens, and cumulative recovery of $^{14}C$. After seven days, 15.9% of the dose was recovered in the urine and stool, consistent with the slow body turnover of vitamin B12.

The time course for the appearance and disappearance of $^{14}$C in plasma over seven days post-dose is presented in FIG. 4. Data is given as femtomols of $^{14}$C-vitamin B12 per mL plasma. After seven hours, the circulating $^{14}$C-B12 reaches a peak in concentration which corresponds to less than three percent of the administered dose of $^{14}$C vitamin B12. The amount of B12 detected at the peak would produce less than one disintegration per minute if assayed by scintillation counting, and thus would be unmeasurable by any decay counting technique. There is a two to three hour delay in the appearance of the label in plasma, consistent with the time taken for gastric emptying and facilitated absorption in the ileum. After the maximum level of $^{14}$C-vitamin B12 was achieved, the concentration of the label decayed at a single rate, with evidence for a small resuspension four days post-dose. FIG. 5 illustrates recovery of the label in urine and stool specimens seven days post-dose. The largest single concentration of label appeared in the twenty-four hour urine collection (6.8% of administered dose). After seven days a total of 15.8% of the oral dose was recovered in urine and feces and 99% of the quantified output was accounted for seventy-two hours post-dose.

Normally, the release of vitamin B12 from intestinal mucosa cells into the portal vein occurs approximately two hours after the oral consumption of the vitamin, while release into systemic circulation takes an additional hour 14. Consistent with this, the $^{14}$C from the labeled vitamin B12 appeared in the plasma of the human subject three hours post-dose. A concentration plateau between five and twelve hours was seen either side of the Cmax, which occurred at seven hours (FIG. 4). This plateau makes it possible to assess vitamin B12 absorption from a single capillary stick blood sample. The current Schilling urinary excretion test, originally introduced in 1953, is rarely prescribed as it requires administration of radiocobalt vitamin B12, followed by an intramuscular flushing dose and twenty four hour total urine collection. In patients with normal absorption, eight to forty percent of the labeled B12 is recovered in the urine, compared to patients with absorption problems, who have almost nil recovery. By contrast, the method we describe has sufficient sensitivity to quantify the $^{14}$C in the urine for 7 days post-dose without a flushing dose, making it possible to follow the fate of the vitamin, at near ambient levels of radiation exposure, using microliter-sized blood specimens.

Example 6

This Example shows how to determine the course of serum levels of B12 in normal patients and those with pernicious anemia using $^{14}$C-labeled B12.

Two cohorts of subjects are selected, one with normal B12 metabolism, and one of persons diagnosed with pernicious anemia. The persons selected for normal B12 metabolism are screened for unrecognized B12 malabsorption or deficiency by measurement of total serum B12, serum methylmalonic acid, total plasma homocysteine, serum gastrin, and serum antibodies to intrinsic factor, as well as for use of supplemental B12, use of drugs that would interfere with B12 absorption, and other factors known to affect B12 absorption or metabolism. Prospective subjects for the pernicious anemia group are previously confirmed by a positive Schilling test, and are also screened as described above.

On day 0, subjects are given a single, oral dose of $^{14}$C-B12 (100 nCi, taken in water) at 7 am., followed by a light breakfast (a banana and a cup of coffee or apple juice). Although the administered B12 is radioactive, subjects will be exposed to a very small amount of radiation (total effective dose equivalent=82 microsieverts). For contrast, one is exposed to 30 microsieverts during a coast-to-coast airline flight.

Blood is drawn at baseline. A catheter is installed in a forearm vein by a registered nurse the morning of dose administration. The catheter is in place for that day only. Subsequent blood draws are made by needle stick. Subjects are asked to forego strenuous physical activities during the first day. Mean volume of blood taken at each time point are ~5 mL (1 teaspoonful). On the first day, blood draws are taken at 0, 1, 2, 4, 6, 8, 12, and 24 hours. Thereafter, blood draws are taken on days 2-5, 7, 10, 14, 21 and 28. Subjects collect complete (cumulative) 24 h urine samples and all stool samples on day 0 (starting 24 h before taking the oral dose of labeled B12) and on each day for 10 days post-dosing (11 samples of each). Plasma and urine are analyzed neat, while stool is dispersed in 0.5 M KOH using a Stomacher mixer. A comparison of the blood levels between the two cohorts at the different time points reveals the time point or points at which the difference is clearest, and the range of values associated with normal absorption and with those having pernicious anemia, respectively.

Example 7

This Example describes simple microbiological tests and controls to determine if a microbe of interest utilizes ethanolamine via a vitamin B12-dependent pathway. The assay below is described in terms of being performed on plates. The conditions of growth for hundreds of bacterial species are known in the art; some are known not to grow on plates, but require growth in flasks or the like. Persons of skill will be aware of the growth conditions known to be optimal for different species and it is anticipated that the assay below can be readily adapted for organisms that cannot be grown on plates.

In the standard assay, four types of standard minimal agar plates are used, as shown below. The plates are augmented to satisfy any auxotrophies that the specific organism, strain or mutant strain of interest is known to have. The test described in Table 2 permits determining whether the organism can grow on ethanolamine as a sole carbon source under aerobic conditions.

TABLE 2 additions to minimal plates

| Plate Type | Description |
|---|---|
| 1 | No further additions made (control, no carbon source, no growth expected) |
| 2 | A user-designated carbon source (e.g.: glucose), known to support growth of the organism under test, is added to the plates at an appropriate concentration (positive control, to show that the organism will grow on a standard carbon source). |
| 3 | Sterile ethanolamine is added to the plates until a final concentration of 40 mM ethanolamine is achieved (if the organism grows on this plate, it indicates it can grow in a vitamin B12 independent manner, and the organism is not of interest for use in the methods). |
| 4 | Sterile ethanolamine is added to the plates to a final concentration of 40 mM. Sterile cyano-B12 is added to the plates to a final concentration of 0.5 µM. (Growth on this plate, but not on plate 3, indicates the organism is of interest for use in the methods.) |

Each of the plates is inoculated from a single bacterial colony in the standard manner (eg: by streaking or by printing from a master plate) and interpreted after growth. Growth will usually take 48 hours at 37° C. The exact temperature and time used will depend on the particular organism's optimal growth characteristics. Growth results are interpreted as shown in Table 3.

TABLE 3

Analysis of plate results

| Result | Plate 1 | Plate 2 | Plate 3 | Plate 4 |
|---|---|---|---|---|
| A. Plates are no good - remake plates | X | − | X | X |
| B. Cannot utilize ethanolamine as sole C source | − | + | − | − |
| C. B12-dependent growth on ethanolamine | − | + | − | + |

TABLE 3-continued

Analysis of plate results

| Result | Plate 1 | Plate 2 | Plate 3 | Plate 4 |
|---|---|---|---|---|
| D. B12-independent growth on ethanolamine | − | + | + | X |
| E. Plates are no good - remake plates | + | X | X | X | key:
− no growth,
+ strong growth,
X growth result ignored on this plate

The organism being assayed must be able to utilize ethanolamine as a sole carbon source for growth, as described in above. The assay requires standard minimal medium agar plates containing, in addition, ethanolamine (40 mM) and dicyanocobinamide (500 nM). The plates must also satisfy any other requirements that a specific organism, strain or mutant strain might have.

TABLE 4 additions to minimal plates

| Plate Type | Description |
|---|---|
| 1 | No DMB added |
| 2 | DMB is added to 500 nM |

If the organism grows on plate 1, the organism can make its own DMB and is unsuitable. Each of the plates is inoculated from a single bacterial colony in the standard manner (eg: by streaking or by printing from a master plate) and is interpreted, after growth, as shown in Table 5. Growth will usually take 48 hours at 37° C. The exact temperature and time used will depend on the particular organism's optimal growth characteristics, which are monitored by appropriate controls.

TABLE 5

Analysis of plate growth

| Result | Plate 1 | Plate 2 |
|---|---|---|
| A. Organism unsuitable | − | − |
| B. Organism unsuitable | + | − |

TABLE 5-continued

Analysis of plate growth

| Result | Plate 1 | Plate 2 |
|---|---|---|
| C. Potentially suitable for substitution | − | + |
| D. Organism unsuitable | + | + | key:
− no growth,
+ strong growth

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining absorption of vitamin B12 in a subject, said method comprising:
   (a) orally administering B12 labeled with $^{14}$C, $^{13}$C, deuterium, or tritium to said subject, wherein the specific activity of the labeled B12 is at least 10 Ci/mol and the B12 mass is less than 10 µg;
   (b) taking a blood sample from said subject,
   (c) subjecting said blood sample to mass spectroscopy and measuring elevation of $^{14}$C, $^{13}$C, or tritium associated with the labeled B12 above background $^{14}$C, $^{13}$C, deuterium, or tritium concentrations, respectively and
   (d) comparing said concentration of labeled B12 found in the subject to the concentration of B12 in subjects with normal B12 absorption to determine the B12 absorption in the subject.

2. A method of claim 1, wherein said mass spectroscopy is accelerator mass spectroscopy.

3. A method of claim 2, wherein said label is $^{14}$C or tritium.

4. A method of studying vitamin B12 metabolism in a subject, said method comprising:
   (a) orally administering B12 labeled with $^{14}$C, $^{13}$C, deuterium, or tritium to said subject, wherein the specific activity of the labeled B12 is at least 10 Ci/mol and the B12 mass is less than 10 µg;
   (b) taking a blood sample from said subject,
   (c) subjecting said blood sample to mass spectroscopy and measuring elevation of $^{14}$C, $^{13}$C, or tritium associated with the labeled B12 above background $^{14}$C, $^{13}$C, deuterium, or tritium concentrations, respectively and
   (d) comparing said concentration of labeled B12 found in the subject to the concentration of B12 in subjects with normal B12 absorption.

5. A method of claim 4, wherein said vitamin B12 metabolism is plasma clearance, turnover rate, enzyme kinetic measurement, or uptake and distribution of the vitamin.

6. The method of claim 1, wherein the $^{14}$C, $^{13}$C, deuterium, or tritium is present on a dimethylbenzimidazole moiety of the labeled B12.

7. The method of claim 1, wherein the specific activity of the labeled B12 is at least 25 Ci/mol.

8. The method of claim 4, wherein the specific activity of the labeled B12 is at least 25 Ci/mol.

* * * * *